United States Patent [19]
Wells

[11] Patent Number: 5,573,709
[45] Date of Patent: Nov. 12, 1996

[54] SHAMPOO COMPOSITIONS WITH SILICONE AND CATIONIC ORGANIC POLYMERIC CONDITIONING AGENTS

[75] Inventor: Robert L. Wells, Cincinnati, Ohio

[73] Assignee: Procter & Gamble, Cincinnati, Ohio

[21] Appl. No.: 388,120

[22] Filed: Feb. 13, 1995

Related U.S. Application Data

[63] Continuation of Ser. No. 129,486, Sep. 29, 1993, abandoned, which is a continuation of Ser. No. 778,765, Oct. 21, 1991, abandoned, which is a continuation of Ser. No. 622,699, Dec. 5, 1990, abandoned.

[51] Int. Cl.$^6$ .............................. C11D 1/65; C11D 1/62; C11D 3/37; C11D 1/82
[52] U.S. Cl. .............................. 510/122; 510/123
[58] Field of Search .............................. 252/547, 550, 252/174.15, DIG. 2, DIG. 13, 174.24

[56] References Cited

U.S. PATENT DOCUMENTS

| | | | |
|---|---|---|---|
| 2,826,551 | 3/1958 | Geen | 252/89 |
| 3,964,500 | 6/1976 | Drakoff | 132/7 |
| 3,969,500 | 7/1976 | Kennerley | 424/10 |
| 3,990,991 | 11/1976 | Gerstein | 252/542 |
| 4,009,256 | 2/1977 | Nowak et al. | 424/70 |
| 4,220,168 | 9/1980 | Newell | 132/7 |
| 4,220,548 | 9/1980 | Hashimoto et al. | 252/106 |
| 4,364,837 | 12/1982 | Pader | 252/173 |
| 4,371,517 | 2/1983 | Vanlerberghe et al. | 424/70 |
| 4,374,125 | 2/1983 | Newell | 424/70 |
| 4,488,564 | 12/1984 | Grollier et al. | 424/70 |
| 4,529,586 | 7/1985 | DeMarco et al. | 424/70 |
| 4,597,962 | 7/1986 | Grollier et al. | 424/47 |
| 4,673,568 | 6/1987 | Grollier et al. | 424/47 |
| 4,704,272 | 11/1987 | Oh et al. | 252/547 |
| 4,707,293 | 11/1987 | Ferro | 252/174.17 |
| 4,710,314 | 12/1987 | Madrange et al. | 252/117 |
| 4,710,374 | 12/1987 | Grollier et al. | 424/61 |
| 4,726,944 | 2/1988 | Osipow et al. | 424/70 |
| 4,728,457 | 3/1988 | Fieler et al. | 252/174.15 |
| 4,741,855 | 3/1988 | Grote et al. | 252/142 |
| 4,749,565 | 6/1988 | Grollier | 424/70 |
| 4,788,006 | 11/1988 | Bolich, Jr. et al. | 252/550 |
| 4,820,308 | 4/1989 | Madrange et al. | 8/405 |
| 4,832,872 | 5/1989 | Scandel | 252/547 |
| 4,842,849 | 6/1989 | Grollier et al. | 132/7 |
| 4,842,850 | 6/1989 | Vu | 424/70 |
| 4,859,456 | 8/1989 | Marschner | 424/47 |
| 4,902,499 | 2/1990 | Bolich et al. | 252/550 |
| 4,906,459 | 3/1990 | Cobb et al. | 424/70 |
| 4,983,383 | 1/1991 | Maksimoski et al. | 424/70 |
| 5,078,990 | 1/1992 | Martin et al. | 424/70 |
| 5,085,857 | 2/1992 | Reid et al. | 424/70 |
| 5,089,252 | 2/1992 | Grollier et al. | 424/97 |
| 5,139,037 | 8/1992 | Grollier et al. | 132/203 |

FOREIGN PATENT DOCUMENTS

| | | |
|---|---|---|
| 0 413 416 | 2/1991 | European Pat. Off. . |
| 0 413 417 | 2/1991 | European Pat. Off. . |
| 0 432 951 A2 | 6/1991 | European Pat. Off. . |
| 54-129135 | 10/1979 | Japan . |
| 55-038813 | 3/1980 | Japan . |
| 56-72095 | 6/1981 | Japan . |
| 327266 | 7/1989 | Japan . |
| 2042008 | 2/1990 | Japan . |
| 2188519 | 7/1990 | Japan . |
| 2188518 | 7/1990 | Japan . |
| 849433 | 9/1960 | United Kingdom . |
| 2161172 | 1/1986 | United Kingdom . |

OTHER PUBLICATIONS

McCutcheon's, Emulsifiers & Detergents; 1981 International Edition p. 188.
Document Number S.N. 07/784,278 Name Wells et al. Filing Date Oct. 29, 1991.
Document Number S.N. 07/622,705 Name Bartz et al. Filing Date Dec. 5, 1990.
McCutcheon's *Emulsifiers & Detergents*, 1981 International Edition, pp. 55 and 157 (no month available).
Caelles, J., Comelles, F., Leal, J. S., Para, J. L. and Anguera, S., "Anionic and Cationic Compounds in Mixed Systems", *Cosmetics & Toiletries*, vol. 106, Apr. 1991, pp. 49–54.
Burgess, D. J., "Practical Analysis of Complex Coacervate Systems", *J. Colloid and Interface Science*, vol. 140, No. 1, Nov. 1990, pp. 227–238.
vanOss, C. J., "Coacervation, Complex–Coacervation and Flocculation", *J. Dispersion Science and Technology*, vol. 9 (Nos. 5 and 6), 1988–1989, (no month available) pp. 561–573.
Amerchol Corp. pamphlet "Quatrisoft® Polymer LM-200". Sep. 1991.

(List continued on next page.)

*Primary Examiner*—Paul Lieberman
*Assistant Examiner*—Erin M. Harriman
*Attorney, Agent, or Firm*—David K. Dabbiere; Anthony D. Sabatelli; Leonard W. Lewis

[57] ABSTRACT

Disclosed are hair conditioning shampoo compositions comprising

A liquid hair conditioning shampoo composition comprising:
(a) from about 5% to about 50%, by weight, of an anionic surfactant component;
(b) from about 0.1% to about 10%, by weight, of a dispersed, insoluble, nonvolatile, nonionic silicone hair conditioning agent;
(c) from about 0.05% to about 10%, by weight, of soluble, organic, polymeric cationic hair conditioning agent, said polymeric, cationic hair conditioning agent consisting essentially of one or more cationic, hair conditioning polymers, said cationic hair conditioning polymers having quaternary ammonium or cationic amino moieties, or a mixture thereof, an open chain backbone, and a charge density of about +3.0 meq/gram or less; and The shampoo compositions hereof can provide excellent overall hair conditioning benefits, in conjunction with excellent cleaning performance, to a variety of hair types including treated hair such as permed and color-treated hair, as well as undamaged hair.

19 Claims, No Drawings

OTHER PUBLICATIONS

McCutcheon's functional Materials 1990, McCutcheon Publishing Co., Glen Rock, NJ, pp. 48, 69. (no month available).

GE Silicones Personal Care Formularies for SS–4230 and SS4267; Skin Care Products— "Principles of Formulating Skin Care Products", SP–102 European Night Cream, SP–103 Moisturizer with Sun Screen, SS–100 Sun Lotion (SPFU), SS–101 Sun Lotion (w/o SPF–4), SS–103 Protective Lip Pomade, and SS–102 Light Oil Sun Screen, General Electric Co., Silicone Products Division.

Hardman and Jorkelson, General Electric Co., "Silicones", reprinted from Eneg. of Polymer Science & Engineering, vol. 15, 2nd Ed., 1989, J. Wiley & Sons, Inc., pp. 265–270. (no month available).

CTFA International Cosmetic Ingredient Dictionary, Fourth Edition, Nikitakis, et al., editors, 1991, pp. 462–463. (no month available).

SHAMPOO COMPOSITIONS WITH SILICONE AND CATIONIC ORGANIC POLYMERIC CONDITIONING AGENTS

This is a continuation of application Ser. No. 08/129,486, filed on Sep. 29, 1993 now abandoned, which is a continuation of application Ser. No. 07/778,765, filed on Oct. 21, 1991, now abandoned, which is a continuation of Ser. No. 07/622,699 filed on Dec. 5, 1990, now abandoned.

FIELD OF THE INVENTION

This invention relates to shampoo compositions comprising anionic detersive surfactants, silicone hair conditioning agents, and cationic polymeric hair conditioning agents.

BACKGROUND OF THE INVENTION

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair is left in a wet, tangled and generally unmanageable state. Shampooing can also result in the hair becoming dry or "frizzy" due to removal of natural of natural oils or other hair moisturizing materials. After shampooing, the hair can also suffer from a loss of "softness" perceived by the user upon drying. A variety of approaches have been developed to alleviate the after-shampoo problems. These range from the inclusion of hair conditioning aids in shampoos to post-shampoo application of hair conditioners, i.e., hair rinses. Hair rinses are generaly liquid in nature and must be applied in a separate step following the shampooing, left on the hair for a length of time, and rinsed with fresh water. This, of course, is time consuming and is not convenient.

While a wide variety of shampoos have been disclosed which contain conditioning aids, they have not been totally satisfactory for a variety of reasons. One problem relates to compatibility problems between good cleaning anionic surfactants and the many conventional cationic agents which historically have been used as conditioning agents, including both carbonic surfactants and cationic polymers.

Whereas efforts have been made to minimize adverse interaction through the use of alternate surfactants and improved cationic conditioning agents, it remains highly desirable to utilize anionic surfactants in shampoo compositions. Furthermore, cationic conditioning agents commonly do not provide optimal overall conditioning benefits, particularly in the area of "softness", especially when delivered as an ingredient in a shampoo composition. Many cationic polymers, additionally, tend to build up on the hair to result in an undesirable, "unclean" coated feel.

Materials which can provide increased softness are non-ionic silicones. Silicones in shampoo compositions have been disclosed in a number of different publications. Such publications include U.S. Pat. No. 2,826,551, Geen, issued Mar. 11, 1958; U.S. Pat. No. 3,964,500, Drakoff, issued Jun. 22, 1976; U.S. Pat. No. 4,364,837, Pader, issued Dec. 21, 1982; and British Patent 849,433, Woolston, issued Sep. 28, 1960. While these patents disclose silicone containing compositions, they also did not provide a totally satisfactory product in that it was difficult to maintain the silicone well dispersed and suspended in the product. Recently, stable, insoluble silicone-containing hair conditioning shampoo compositions have been described in U.S. Pat. No. 4,741,855, Grote and Russell, issued May 3, 1988 and U.S. Pat. No. 4,788,006, Bolich and Williams, issued Nov. 29, 1988. These shampoo compositions can deliver excellent overall conditioning benefits to the hair while maintaining excellent cleaning performance, even with the use of anionic detersive surfactants, for a wide variety of hair types. However, it would be desirable to improve these types of shampoos such that they provided improved conditioning benefits to one type of hair in particular, that type being hair damaged by permanent treatments (i.e., "perms"), color treatments, and bleach treatments, applied either at hair salons or at home. Unfortunately, silicone hair conditioner efficacy for permed hair appears to be lower than that for most undamaged hair. It would be desirable to provide a shampoo composition that would provide excellent overall cleaning and conditioning benefits for such hair, as well as other types of hair not subjected to such treatments. This would reduce the need for families or other residents to purchase separate hair conditioning shampoo products for persons with damaged and undamaged hair.

It is an object of this invention to provide shampoo compositions, which can provide excellent cleaning performance and excellent overall hair conditioning for such damaged hair as well as for hair not subjected to such treatments ("undamaged hair").

It is a further object of this invention to provide an improved anionic surfactant-containing shampoo compositions that can provide excellent cleaning performance and conditioning performance for both damaged and undamaged hair types, such that the shampooed hair can have desirable levels of manageability, combability, softness, and low or reduced levels of dryness.

These objects will become apparent from the description which follows, as many other objects become apparent upon a reading of said description.

Unless otherwise indicated, all percentages are calculated by weight of the total composition, and all ratios are calculated on a weight basis.

SUMMARY OF THE INVENTION

This invention provides anionic detersive surfactant-containing liquid shampoo compositions that can provide both excellent cleaning performance and hair conditioning benefits to a wide variety of hair types, including treatment damaged and undamaged hair. This can be attained by incorporating into the shampoo composition a nonionic, insoluble, nonvolatile silicone hair conditioning agent and, additionally, a critically selected soluble, organic, cationic, polymeric conditioning agent. The shampoo compositions hereof will also comprise an aqueous carrier.

The cationic polymer conditioning agents of the present invention are organic polymers having quaternary ammonium or amino moieties (said amino moieties being cationic at the pH of the shampoo composition which is generally between about pH 2 and pH 10, more preferably from about pH 3 to about pH 9) and are characterized by an open chain backbone. Furthermore, these polymers essentially have a charge density of about +3.0 meq/gram or less, preferably about +2.75 meq/gram or less. The precise cationic charge density is not believed to be critical as long as it is less than those stated essential and preferred limits. However, for practical reasons, the charge density should be of a level such that efficient substantivity between the polymer and the hair can be attained. Generally, it is preferred that cationic charge density be at least about 0.2 meq/gram, more preferably at least about 0.4 meq/gram.

When combined with the nonionic silicone conditioning agents in the shampoo compositions of this invention, these cationic organic polymers can provide surprisingly good hair conditioning benefits for permed or other damaged hair characterized by increased anionic character, such as bleached hair and color treated hair. These types of hair that have been damaged and are characterized by increased anionic character shall hereinafter be collectively referred to as "damaged hair". Nonionic silicone conditioning agents suffer from reduced deposition, and therefore reduced efficacy, for these hair types. On the other hand, the use of the cationic organic polymers as the sole type of hair conditioning agents to damaged hair and especially to undamaged hair when delivered from shampoo compositions may not provide sufficient overall conditioning benefits, especially in the area of softness. The combination of hair conditioning agents, however, results in shampoo compositions with high levels of conditioning for damaged hair, and retains excellent conditioning for undamaged hair and cleaning performance for all hair types. As used herein, undamaged refers to hair that is not damaged by perms or other hair treatments which increase the anionic character of the hair, and does not exclude, for example, oily hair, dry hair, etc., or hair damaged in some other respect, unless such other damage is specifically and expressly indicated. These performance benefits are especially important because merely increasing the level of silicone conditioning agent in a particular shampoo that is effective for treating undamaged hair to improve conditioning of damaged hair can result in too high a level of silicone deposition for undamaged hair. This can impart an undesirable greasy feel. On the other hand, the cationic organic polymer, by itself, does not provide efficient conditioning of undamaged hair. The present invention provides anionic detersive surfactant-containing shampoo compositions that can provide excellent conditioning to both damaged and normal hair through the use of nonionic silicone and particularly selected soluble, organic, polymeric, cationic conditioning agents hereof.

Although it is not intended to limit the present invention by theory, it is believed that the cationic polymers of the present invention are particularly advantageous for use in anionic detersive surfactant-containing shampoos as a result of a combination of factors. First is the absence of ring structures in the polymer backbone. This type of backbone results in a more flexible polymer which, along with their relatively low charge density, reduces the tendency of many cationic polymers to undesirably build up on the hair upon repeated usage. The use of these cationic, organic polymers as conditioning agents along with the silicone conditioning agents hereof can provide excellent cleaning shampoos useful for conditioning a wide variety of damaged and undamaged hair types.

In a preferred embodiment, the present invention provices hair conditioning shampoo compositions comprising:
(a) from about 5% to about 50%, by weight, of an anionic detersive surfactant component;
(b) from about 0.1% to about 10%, by weight, of a dispersed, insoluble, nonvolatile, nonionic silicone conditioning agent;
(c) from about 0.05% to about 10%, by weight, of soluble, organic, polymeric, cationic hair conditioning agent, said polymeric, cationic hair conditioning agent consisting essentially of one or more cationic hair conditioning polymers, said cationic hair conditioning polymers having quaternary ammonium or cationic amino moieties, or a mixture thereof, an open chain backbone, and a charge density of about +3.0 meq/gram or less; and
(d) an aqueous carrier.

As used herein, the terms "soluble" and "insoluble" used in reference to particular ingredients of the shampoo compositions refer to solubility or insolubility, respectively, of that ingredient in the shampoo composition.

All percentages are calculated by weight of the total composition unless otherwise specifically indicated.

The invention, including preferred embodiments thereof, is described in further detail in the Detailed Description of the Invention, which follows.

DETAILED DESCRIPTION OF THE INVENTION

The essential as well as a variety of preferred and optional components of the compositions of the present invention are described below.

Anionic Detersive Surfactant

The hair conditioning shampoo compositions of the present invention comprise an anionic detersive surfactant to provide cleaning performance to the composition.

The anionic detersive surfactant will generally be from about 5% to about 50%, preferably from about 8% to about 30%, more preferably from about 10% to about 25%, of the composition. The anionic detersive surfactant of the compositions hereof can be a single species of surfactant or a combination of different surfactants.

Synthetic anionic detersive detergents useful herein include alkyl and alkyl ether sulfates. These materials have the respective formulae $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. The alkyl ether sulfates are typically made as condensation products of ethylene oxide and monohydric alcohols having from about 8 to about 24 carbon atoms. Preferably, R has from about 12 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide. Such a mixture also comprises from about 0 to about 20% by weight $C_{12-13}$ compounds; from about 60 to about 100% by weight of $C_{14-15-16}$ compounds, from about 0 to about 20% by weight of $C_{17-18-19}$ compounds; from about 3 to about 30% by weight of compounds having a degree of ethoxylation of 0; from about 45 to about 90% by weight of compounds having a degree of ethoxylat ion of from about 1 to about 4; from about 10 to about 25% by weight of compounds having a degree of ethoxylation of from about 4 to about 8; and from about 0.1 to about 15% by weight of compounds having a degree of ethoxylation greater than about 8.

Another suitable class of anionic detersive surfactants are the water-soluble salts of the organic, sulfuric acid reaction products of the general formula:

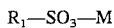

wherein $R_1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$ n-paraffins.

Additional examples of synthetic anionic detersive surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other synthetic anionic detersive surfactants of this variety are set forth in U.S. Pat. Nos. 2,486,921; 2,486,922; and 2,396,278.

Still other synthetic anionic detersive surfactants are in the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Other suitable anionic detersive surfactants utilizable olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having about 12 to about 24 carbon atoms, preferably about 14 to about 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific α-olefin sulfonate mixture of the above type is described more fully in the U.S. Pat. No. 3,332,880 Pflaumer and Kessler, issued Jul. 25, 1967, incorporated herein by reference.

Another class of anionic detersive surfactants are the β-alkyloxy alkane sulfonates. These compounds have the following formula:

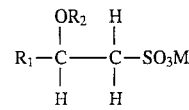

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Specific examples of β-alkyloxy-alkane-1-sulfonates, or alternatively 2-alkyloxy-alkane-1-sulfonates, having low hardness (calcium ion) sensitivity useful herein include: potassium-β-methoxydecanesulfonate, sodium 2-methoxy-tridecanesulfonate, potassium 2-ethoxytetradecylsulfonate, sodium 2-isopro-poxyhexadecylsulfonate, lithium 2-t-butoxytetradecyl-sulfonate, sodium β-methoxyoctadecylsulfonate, and ammonium β-n-propoxydodecylsulfonate.

Many additional synthetic anionic surfactants are described in *McCutcheon's, Emulsifiers and Detergents, 1989 Annual*, published by M. C. Publishing Co., which is incorporated herein by reference. Also U.S. Pat. No. 3,929,678, Laughlin et al., issued Dec. 30, 1975, discloses many other anionic as well as other surfactant types and is incorporated herein by reference.

Preferred anionic detersive surfactants for use in the present shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Optional Detersive Surfactants

In addition to the anionic detersive surfactant, the compositions of the present invention can optionally contain other detersive surfactants. These include nonionic surfactants, amphoteric surfactants, zwitterionic surfactants. Optional detersive surfactants, when used, are typically present at levels of from about 0.5% to about 20%, more typically from about 1% to about 10%. Also, the total amount of detersive surfactant in compositions containing optional detersive surfactants in addition to the anionic surfactant will generally be from about 5.5% to about 50%, preferably from about 8% to about 30%, more preferably from about 10% to about 25%. Cationic detersive surfactants can also be used, but are generally less preferred because they can adversely interact with the anionic detersive surfactant. Cationic detersive surfactants, if used, are preferably used at levels no greater than about 5%.

Nonionic detersive surfactants which can be used include those broadly defined as compounds produced by the condensation of alkylene oxide groups (hydrophilic in nature)

with an organic hydrophobic compound, which may be aliphatic or alkyl aromatic in nature. Examples of preferred classes of nonionic detersive surfactants are 1. The polyethylene oxide condensates of alkyl phenols, e.g., the concensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

$$R_1R_2R_3N \rightarrow 0$$

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

$$RR'R''P \rightarrow 0$$

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide. 3,6,9,-trioxaoctadecyldimethylphosphine oxide, cetyldimethylphosphine oxide, 3-dodecoxy-2-hydroxypropyldi (2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Zwitterionic detersive surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$R^2-Y^{(+)}(R^3)_x-CH_2-R^4-Z^{(-)}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1- sulfate;

3-[P,P-diethyl-P-3,6,9-trioxatetradexocylphosphonio]-2-hydroxy-propane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1- sulfonate;

4-[N,N-di(2-hydroxyethyl)-N-(2-hydroxydodecyl)ammonio ]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Other zwitterionics such as betaines can also useful in the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the 1 like; amidobetaines and amidosulfobetaines, wherein the $RCONH(CH_2)_3$ radical is attached to the nitrogen atom of the betaine are also useful in this invention. Preferred betaines for use in the present compositions are cocoamidopropyl betaine, cocobetaine, lauryl amidopropyl betaine, and oleyl betaine.

Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL"™ and described in U.S. Pat. No. 2,528,378. Another deteresive surfactant optional for use in the compositions of the present invention is cocoamphocarboxy glycinate.

The most preferred shampoos of the present invention contain specific combinations of anionic surfactants, zwitterionic surfactants, and amphoteric surfactants. The preferred shampoos contain from about 2% to about 16% of alkyl sulfates, from 0% to about 14% of ethoxylated alkyl sulfates, and from about 0% to about 10% of an optional detersive surfactant selected from the nonionic, amphoteric, and zwitterionic detersive surfactants, with a total surfactant level of from about 10% to about 25%.

Silicone Hair Conditioning Agent

An essential component of the present invention is a volatile, nonionic silicone hair conditioning agent which is insoluble in the shampoo compositions hereof. The silicone conditioning agent comprises a silicone fluid component which contains a nonvolatile, insoluble, silicone fluid and optionally comprises a silicone gum which is insoluble in the shampoo composition as a whole but is soluble in the silicone fluid. The silicone hair conditioning agent can also comprise a silicone resin to enhance silicone fluid component deposition efficiency.

The silicone hair conditioning agent may comprise low levels of volatile silicone components; however, such volatile silicones will preferably exceed no more than about 0.5%, by weight, of the shampoo composition. Typically, if volatile silicones are present, it will be for practical reasons incidental to their utility as a solvent and carrier for commercially available silicone resins.

The silicone hair conditioning agent for use herein will preferably have viscosity of from about 1,000 to about 2,000,000 centistokes at 25° C., more preferably from about 10,000 to about 1,800,000, even more preferably from about 100,000 to about 1,500,000. The viscosity can be measured by means of a glass capillary viscometer as set forth in Dow Corning Corporate Test Method CTM0004, Jul. 20, 1970.

The silicone. hair conditioning agent will be used in the shampoo compositions hereof at levels of from about 0.1% to about 10% by weight of the composition, preferably from about 0.5% to about 8%, more preferably from about 1% to about 5%.

Suitable insoluble, nonvolatile silicone fluids include polyalkyl siloxanes, polyaryl siloxanes, polyalkylaryl siloxanes, polyether siloxane copolymer and mixtures thereof. However, other insoluble, nonvolatile silicone fluids having hair conditioning properties may be used. The term "nonvolatile" as used herein shall mean that the silicone material exhibits very low or no significant vapor pressure at ambient conditions, as is well understood in the art. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000. The term "silicone", as used herein, shall be synonomous with the term "polysiloxane".

The nonvolatile polyalkylsiloxane fluids that may be used include, for example, polydimethyl siloxanes. These siloxanes are available, for example, from the General Electric Company as a Viscasil series and from Dow Corning as the Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified dimethylpolysiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Silicone fluids hereof also include polyalkyl or polyaryl siloxanes with the following structure:

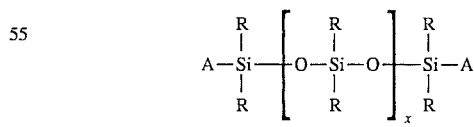

wherein R is alkyl or aryl, and x is an integer from about 7 to about 8,000 may be used. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irratating, toxic nor othewise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; and British Patent 849,433, Woolston. All of these patents are incorporated herein by reference. Also incorporated herein by reference is *Silicon Compounds* distributed by Petrarch Systems, Inc., 1984. This reference provides an extensive (though not exclusive) listing of suitable silicone fluids.

Another silicone material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, *Chemistry and Technology of Silicones,* New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Preferably the silicone hair conditioning agent comprises a mixture of a polydimethylsiloxane gum, having a viscosity greater than about 1,000,000 centistokes and polydimethylsiloxane fluid having a viscosity of from about 10 centistokes to about 100,000 centistokes, wherein the ratio of gum to fluid is from about 30:70 to about 70:30, preferably from about 40:60 to about 60:40.

Another optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, monomer units during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, monophenyl-, diphenyl-, methylphenyl-, monovinyl-, and and methylvinyl-chlorosilanes, and tetra-chlorosilane, with the methyl-substituted silanes being most commonly utilized. Preferred resins are offered by General Electric as GE SS4230 and SS4267. Commercially available silicone resins will generally be supplied in an unhardened form in a low viscosity volatile or nonvolatile silicone fluid. The silicone resins for use herein should be supplied and incorporated into the present compositions in such unhardened form, as will be readily apparent to those skilled in the art.

Background material on silicones including sections discussing silicone fluids, gums, and resins, as well as manufacture of silicones, can be found in *Encyclopedia of Polymer Science and Engineering,* Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid component to the silicone resin component is from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above.

Polymeric, Cationic Hair Conditioning Agent

The shampoo compositions of the present invention comprise a soluble, organic, polymeric cationic hair conditioning agent as an essential element. The polymeric cationic hair conditioning agent hereof will generally be present at levels of from about 0.05% to about 10%, preferably from about 0.1% to about 5%, more preferably from about 0.3% to about 3%, by weight, of the shampoo composition.

The cationic organic polymers useful in the hair conditioning agent hereof are organic polymers that can provide conditioning benefits to hair and that are soluble in the shampoo composition. Structurally, these polymers are characterized by open chain backbone, with quaternary ammonium or cationic amino moieties, or a mixture thereof, and a charge density which is no greater than about +3.0 meq/gram. Preferably, charge density is less than about +2.75 meq/gram. The precise cationic charge density is not believed to be critical so long as it is less than those stated essential and preferred limits. However, for practical reasons, the charge density should be of a level such that efficient substantivity between the polymer and the hair can be attained. Generally, it is preferred that cationic charge density be at least about 0.2 meq/gram, more preferably at least about 0.4 meq/gram. Generally, the shampoo pH will be between about 3 and about 9, preferably between about 4 and about 8. Those skilled in the art will recognize that the charge density of amino-containing polymers may vary depending upon pH and the isoelectric point of the amino groups. Additionally, it is preferred that the charge density be within the above limits at the pH of intended use which will, in general, be from about pH 4 to about pH 9, most generally from about pH 5 to about pH 8. The polymer, of course, must remain cationic upon application to the hair in order for there to be adequate substantivity between the conditioning agent and the hair.

The cationic hair conditioning polymers hereof have a flexible, open chain organic backbone comprising saturated carbon-carbon covalent bonds. The polymer backbones are preferably substantially free of carbon-carbon triple bonds, which can adversely affect polymer flexibility. More preferably, the polymer backbone will be completely free of carbon-carbon triple bonds.

The cationic nitrogen-containing moiety will be present generally as a substituent, on a fraction of the total monomer units of the cationic hair conditioning polymers. Thus, the cationic can comprise copolymers, terpolymers, etc. of quaternary ammonium or cationic amine-substituted monomer units and other non-cationic units referred to herein as spacer monomer units. Such materials are known in the art, and a variety of such materials can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982). As used herein, the term "polymer" shall include materials whether made by polymerization of one type of monomer as well as materials made by two (i.e., copolymers) or more types of monomers.

Suitable cationic polymers include, for example, copolymers of vinyl monomers having cationic amine or quaternary ammonium functional ities with water soluble spacer monomers such as acylamide, methacrylamide, alkyl and dialkyl acrylamides, alkyl and dialkyl methacrylamides, alkyl acrylate, alkyl methacrylate, vinyl caprolactone, and N-vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

Tertiary amine-substituted vinyl monomers can be polymerized in the amine form, or can be converted to ammonium by a quaternization reaction. The amines can also be similarly quaternized subsequent to formation of the polymer.

Tertiary amine functional ities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium. X can be, for example, a halide (e.g., Cl, Br, I, or F, preferably Cl, Br, or I) or a sulfate.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, vinyl quaternary ammonium monomers having cyclic cationic nitrogen-containing rings such as pyridinium and imidazolium, e.g., alkyl vinyl imidazolium and alkyl vinyl pyridinium salts. The alkyl portions of these monomers are preferably lower alkyls such as the $C_1$–$C_3$ alkyls, more preferably $C_1$ and $C_2$ alkyls. The quaternary ammonium salts must, of course, be soluble, and the anionic counterions referred to above are suitable.

The amine-substituted monomers useful for cationic organic polymers hereof will preferably be secondary or tertiary amines, more preferably tertiary amines. Suitable amine-substituted vinyl monomers for use herein include dialkylaminoalkyl acrylate, dialkylaminoalkyl methacrylate, dialkylaminoalkyl acrylamide, dialkylaminoalkyl and methacrylamide wherein the alkyl groups are preferably $C_1$–$C_7$, more preferably $C_1$–$C_3$, alkyls.

The cationic polymers hereof can also comprise mixtures of monomer units derived from amine and/or quaternary ammonium-substituted oxyalkylene, vinyl, or other polymerizable monomer and compatible spacer monomers.

The charge density, i.e., the meq/gram of cationic charge, can be controlled and adjusted in accordance with techniques will known in the art. In general, adjustment of the proportions of amine or quaternary ammonium moieties in the polymer, as well as pH of the shampoo composition in the case of the amines, will affect the charge density.

Specific examples of suitable cationic hair conditioning polymers include, for example, copolymers of 1-vinyl-2-pyrrolidone and 1-vinyl-3-methylimidazolium salt (e.g., chloride salt) (referred to in the industry as Polyquaternium-16), such as those commercially available from BASF Wyandotte Corp. (Parsippany, N.J., USA) under LUVIQUAT tradename (e.g., LUVIQUAT FC 370) and copolymers of 1-vinyl-2-pyrrolidone and dimethylaminoethyl methacrylate (referred to in the industry as Polyquaternium-11) such as those commercially available from Gaf Corporation (Wayne, N.J., USA) under the GAFQUAT tradename (e.g., GAFQUAT 755N).

Aqueous Carrier

The shampoo compositions of the present invention are liquids which, preferably are pourable at room temperature. The compositions hereof will comprise an aqueous carrier, i.e., water, which will generally be present at a level of about 20% to about 95% by weight of the composition, preferably from about 60% to about 85% for pourable, liquid formulations. The compositions of the present invention can also be in other forms, such as gels, mouse, etc. In such cases, appropriate components known in the art such as gelling agents (e.g., hydroxyethyl cellulose), etc. can be included in the compositions. Gels will typically contain from about 20% to about 90% water. Mousses will contain aerosol propellent in a low viscosity composition qnd are packaged in an aerosol can, according to techniques well known in the art.

Suspending Agent for Silicone Conditioning Agent

Since the silicone conditioning agent used in the present compositions is an insoluble silicone dispersed in the compositions, it is preferred to utilize a suspending agent for the silicone. Suitable suspending agents are long chain acyl derivatives, long chain amine oxides, and mixtures thereof, wherein such suspending agents are present in the shampoo compositions in crystalline form. A variety of such suspending agents are described in U.S. Pat. No. 4,741,855, Grote et al., issued May 3, 1988. Especially preferred is ethylene glycol distearate.

Also included among the long chain acyl derivatives useful as suspending agents are the N,N-di(hydrogenated) $C_{16}$–$C_{18}$ amido benzoic acid, or soluble salt (e.g., K, Na salts) thereof particularly N,N-di(hydrogenated)tallow amido benzoic acid which is commercially marketed by Stepan Company (Northfield, Ill., USA).

Another useful suspending agent for the silicone conditioning agents of the present compositions is xanthan gum as described in U.S. Pat. No. 4,788,006, Bolich et al., issued Nov. 29, 1988. The combination of long chain acyl derivatives and xanthan gum as a suspending system for silicone is described in U.S. Pat. No. 4,704,272, Oh et al., issued Nov. 3, 1987, and may also be used in the present compostions.

Generally, the shampoo compositions will comprise from about 0.1% to about 5.0%, preferably from about 0.5% to about 3.0%, of the suspending agent to suspend the silicone conditioning agent.

Optional Components

The present compositions may also comprise a variety of non-essential, optional shampoo components suitable for rendering such compositions more cosmetically or aesthetically acceptable or to provide them with additional usage benefits. A variety of such ingredients are well-known to those skilled in the art, and these include without limiting the invention thereto: pearlescent aids, such as $tiO_2$ coated mica, ethylene glycol distearate; opacifiers; preservatives, such as benzyl alcohol, 1,3-bis(hydroxymethyl )-5,5-dimethyl-2,3-imidazolidinedione (e.g., Glydant®, Glyco, Inc., Greenwich, Conn, USA), methylchloroisothiazol inone (e.g., Kathon®, Rohm & Haas Co., Philadelphia, Pa., USA), methyl paraben, propyl paraben, and imidazolidinyl urea; fatty alcohols, such as cetearyl alcohol, cetyl alcohol, and stearyl alcohol; sodium chloride; sodium sulfate; ethyl alcohol; pH adjusting aids, such as citric acid, sodium citrate, succinic acid, phosphoric acid, monosodium phosphate, disodium phosphate, sodium hydroxide, and sodium carbonate; coloring agents or dyes; perfumes; and sequestering agents, such as disodium ethylenediamine tetra-acetate.

Another optional ingredient that can be advantageously used is an anti-static agent. The anti-static agent should not unduly interfere with the in-use performance and end-benefits of the shampoo; particularly, the anti-static agent should not interfere with the anionic detersive surfactant. Suitable anti-static agents include, for example, tricetyl methyl ammonium chloride.

Typically, from about 0.1% to about 5% of such anti-static agent is incorporated into the shampoo compositions.

Though the silicone suspending agent component may act to thicken the present compositions to some degree, the present compositions may also optionally contain other thickeners and viscosity modifiers such as an ethanolamide of a long chain fatty acid (e.g., polyethylene (3) glycol lauramide and coconut monoethanolamide).

These optional components generally are used individually in the compositions of the present invention at a level of from about 0.01% to about 10%, preferably from about 0.05% to about 5.0% of the shampoo composition.

The pH of the present compositions will generally be in the range of from about 2 to about 10, preferably from about 3 to about 9.

Method of Manufacture

The compositions of the present invention, in general, can be made by mixing the materials together at elevated temperature, e.g., about 72° C. The silicone resin, if any, and silicone fluid component are first mixed together before being mixed with the other ingredients. The complete mixture is mixed thoroughly at the elevated temperature and is then pumped through a high shear mill and then through a heat exchanger to cool it to ambient temperature. The average particle size of the silicone is preferably from about 0.5 microns to about 20 microns. Alternately, the silicone conditioning agent can be mixed with anionic surfactant and fatty alcohol, such as cetyl and stearyl alcohols, at elevated temperature, to form a premix containing dispersed silicone. The premix can then be added to and mixed with the remaining materials of the shampoo, pumped through a high shear mill, and cooled.

Method of Use

The shampoo compositions of the present invention are utilized conventionally, i.e., the hair is shampooed by applying an effective amount of the shampoo composition to the scalp, and then rinsing it out. Application of the shampoo to the scalp in general, encompasses massaging or working the shampoo in the hair such that all or most of the hair on the scalp is contacted. The term an "effective amount" as used herein, is an amount which is effective in cleaning and conditioning the hair. Generally, from about 1 g to about 20 g of the composition is applied for cleaning and conditioning the hair.

EXAMPLES

The following examples illustrate the present invention. It will be appreciated that other modifications of the present invention within the skill of those in the hair care formulation art can be undertaken without departing from the spirit and scope of this invention.

All parts, percentages, and ratios herein are by weight unless otherwise specified. Some components may come from suppliers as dilute solutions. The levels given reflect the active weight percent of such materials.

Example I

The following is a shampoo composition of the present invention.

| Component | Weight % |
| --- | --- |
| Ammonium Lauryl Sulfate | 13.5 |
| Ammonium Laureth (3) Sulfate | 4.0 |
| LUVIQUAT FC 370[1] | 0.5 |
| Coconut Monoethanol Amide | 1.0 |
| Ethylene Glycol Distearate | 1.5 |
| Ammonium Xylene Sulfonate | 1.0 |
| Xanthan Gum | 0.5 |
| Polydimethylsiloxane[2] | 3.0 |
| Cetyl Alcohol | 0.4 |
| Stearyl Alcohol | 0.2 |
| Perfume | 1.2 |

-continued

| Component | Weight % |
|---|---|
| Color Solution | 0.6 |
| Preservative | 0.2 |
| Water and Minors | 72.4 |

[1]Tradename of BASF Wyandotte Corporation (Parsippany, NJ, USA) for copolymer of vinyl pyrrolidone and methyl vinyl imidazolium chloride.
[2]A 40/60 weight ratio blend of polydimethylsiloxane gum (GE SE 76, available from General Electric Co., Silicone Products Div., Waterford, NY, USA) and polydimethylsiloxane fluid (about 350 centistokes).

The composition can provide excellent in-use hair cleaning and conditioning, for both damaged and undamaged, or normal, hair types.

Example II

The following is an example of a shampoo composition of the present invention.

| Component | Weight % |
|---|---|
| Ammonium Lauryl Sulfate | 13.0 |
| Ammonium Laureth (3) Sulfate | 5.0 |
| GAFQUAT 755N[1] | 0.5 |
| Coconut Monoethanol Amide | 1.5 |
| Ethylene Glycol Distearate | 2.0 |
| Ammonium Xylene Sulfonate | 1.0 |
| Polydimethylsiloxane[2] | 2.5 |
| Cetyl Alcohol | 0.4 |
| Stearyl Alcohol | 0.2 |
| Perfume | 1.2 |
| Color Solution | 0.6 |
| Preservative | 0.2 |
| Water and Minors | 71.9 |

[1]Tradename of Gaf Corporation (Wayne, New Jersey, USA) for copolymer of vinyl pyrrolidone and ethyl dimethyl methacryoxyethyl ammonium methosulfate.
[2]A 40/60 weight ratio blend of polydimethylsiloxane gum (GE SE 76, available from General Electric Co., Silicone Products Div., Waterford, NY, USA) and polydimethylsiloxane fluid (about 350 centistokes).

The composition can provide excellent in-use hair cleaning and conditioning, for both damaged and undamaged, or normal, hair types.

Example III

The following is an example of a shampoo composition of the present invention.

| Component | Weight % |
|---|---|
| Ammonium Lauryl Sulfate | 13.5 |
| Ammonium Laureth (3) Sulfate | 4.0 |
| LUVIQUAT FC 370[1] | 0.5 |
| Coconut Monoethanol Amide | 1.5 |
| Ethylene Glycol Distearate | 2.0 |
| Trimethylsiloxysilicate | 0.1 |
| Polydimethylsiloxane[2] | 2.0 |
| Cetyl Alcohol | 0.4 |
| Stearyl Alcohol | 0.2 |
| Perfume | 1.2 |
| Color Solution | 0.6 |
| Preservative | 0.2 |
| Water and Minors | 73.8 |

[1]Tradename of BASF Wyandotte Corporation (Parsippany, NJ, USA) for copolymer of vinyl pyrrolidone and methyl vinyl imidazolium chloride.
[2]A 40/60 weight ratio blend of polydimethylsiloxane gum (GE SE 76, available from General Electric Co., Silicone Products Div., Waterford, NY, USA) and polydimethylsiloxane fluid (about 350 centistokes).

The composition can provide excellent in-use hair cleaning and conditioning, for both damaged and undamaged, or normal, hair types.

Example IV

The following is an example of a shampoo composition of the present invention.

| Component | Weight % |
|---|---|
| Ammonium Lauryl Sulfate | 4.0 |
| Cocoamidopropyl Betaine | 3.5 |
| Ammonium Laureth (3) Sulfate | 9.0 |
| Sodium N-Lauryl β-Iminodipropionate | 4.0 |
| LUVIQUAT FC 370[1] | 0.3 |
| Coconut Monoethanol Amide | 2.0 |
| Ethylene Glycol Distearate | 2.0 |
| Xanthan Gum | 0.5 |
| Polydimethylsiloxane[2] | 2.0 |
| Cetyl Alcohol | 0.4 |
| Stearyl Alcohol | 0.2 |
| Perfume | 1.2 |
| Color Solution | 0.6 |
| Preservative | 0.2 |
| Water and Minors | 70.4 |

[1]Tradename of BASF Wyandotte Corporation (Parsippany, NJ, USA) for copolymer of vinyl pyrrolidone and methyl vinyl imidazolium chloride.
[2]A 40/60 weight ratio blend of polydimethylsiloxane gum (GE SE 76, available from General Electric Co., Silicone Products Div., Waterford, NY, USA) and polydimethylsiloxane fluid (about 350 centistokes).

Example V

The following is a shampoo composition of the present invention.

| Component | Weight % |
|---|---|
| Ammonium Lauryl Sulfate | 13.5 |
| Ammonium Laureth (3) Sulfate | 4.0 |
| LUVIQUAT FC 370[1] | 0.5 |
| Coconut Monoethanol Amide | 1.0 |
| Ethylene Glycol Distearate | 2.0 |
| Ammonium Xylene Sulfonate | 1.4 |
| Polydimethylsiloxane Fluid Component[2] | 2.85 |
| MQ Silicone Resin/Volatile Cyclomethicone[3] | .15 |
| Cetyl Alcohol | 0.4 |
| Stearyl Alcohol | 0.2 |
| Perfume | 1.2 |
| Color Solution | 0.6 |
| Preservative | 0.03 |
| Water and Minors | to 100% |

[1]Tradename of BASF Wyandotte Corporation (Parsippany, NJ, USA) for copolymer of vinyl pyrrolidone and methyl vinyl imidazolium chloride.
[2]A 40/60 weight ratio blend of polydimethylsiloxane gum (GE SE 76, available from General Electric Co., Silicone Products Div., Waterford, NY, USA) and polydimethylsiloxane fluid (about 350 centistokes).
[3]A 60/40 weight ratio belnd of the MQ resin in volatile silicone carrier. M:Q molar ratio of about 0.8:1.0.

The composition can provide excellent in-use hair cleaning and conditioning, for both damaged and undamaged, or normal, hair types.

The compositions hereof can be made by preparing a premix of the entire amount of silicone conditioning agent (i.e., the silicone fluid component and the silicone resin) to be incorporated into the shampoo, along with sufficient ammonium laureth sulfate and cetyl and stearyl alcohol such that the premix comprises about 30% silicone conditioning agent, about 69% surfactant, and about 1% of the alcohols. The premix ingredients are heated and stirred at 72° C. for about 10 minutes and the premix is then conventionally mixed with the remaining hot ingredients. The composition is then pumped through a high shear mixer and cooled.

What is claimed is:

1. A liquid hair conditioning shampoo composition comprising:

(a) from about 5% to about 50%, by weight, of an anionic surfactant component;

(b) from about 0.1% to about 10%, by weight, of a dispersed, insoluble, nonvolatile, nonionic silicone hair conditioning agent;

(c) from about 0.05% to about 10%, by weight, of a soluble, organic, cationic hair conditioning polymer having an open chain backbone and a charge density of about +3.0 meq/gram or less, said cationic hair conditioning polymer being a copolymer of water soluble n-vinyl pyrrolidone spacer monomers and cationic vinyl quaternary ammonium monomers selected from the group consisting of halide and sulfate salts of $C_1$–$C_3$ alkyl vinyl pyridinium and $C_1$–$C_3$ alkyl vinyl imidazolium; and (d) an aqueous carrier.

2. A liquid hair conditioning shampoo composition as in claim 1, further comprising a suspending agent for said silicone hair conditioning agent.

3. A shampoo composition as in claim 2, wherein said cationic hair conditioning polymer is a copolymer of 1-vinyl-2-pyrrolidone and 1-vinyl-3-methylimidazolium salt.

4. A shampoo composition as in claim 2, further comprising from about 0.5% to about 20% of a detersive surfactant selected from the group consisting of nonionic, zwitterionic, and amphoteric surfactants, and mixtures thereof.

5. A shampoo composition as in claim 2, wherein said anionic detersive surfactant component is selected from the group consisting of alkyl sulfates, ethoxylated alkyl sulfates, and mixtures thereof.

6. A shampoo composition as in claim 2 wherein the surfactant is selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, aluric monoglyceride sodium sulfate, sodium lauryl sulfate, sodium laureth sulfate, potassium lauryl sulfate, potassium laureth sulfate, lauryl sapcosine, cocoyl sapcosine, ammonium cocoyl sulfate, ammonium lauroyl sulfate, sodium cocoyl sulfate, sodium lauroyl sulfate, potassium cocoyl sulfate, potassium lauroyl sulfate, triethanolamine lauroyl sulfate, sodium tridecyl benzene sulfonate, sodium dodecyl benzene sulfonate, and mixtures thereof.

7. A shampoo composition as in claim 2, further comprising from about 0.1% to about 20% of a detersive surfactant selected from the group consisting of nonionic, zwitterionic, and amphoteric surfactants, and mixtures thereof.

8. A shampoo composition as in claim 7 wherein the composition comprises a detersive surfactant selected from the group consisting of betaines, sarcosinates, cocoamphocarboxy glycinate, and mixtures.

9. A shampoo composition as in claim 2 wherein the silicone conditioning agent is present at a level of from about 0.5% to about 10%.

10. A shampoo composition as in claim 9 wherein the silicone conditioning agent is present at a level of from about 0.5% to about 5% and comprises a silicone fluid component containing polydimethylsiloxane gum having a viscosity greater than about 1,000,000 centistokes at 25° C. and a polydimethylsiloxane fluid having a viscosity of from about 10 centistokes to about 100,000 centistokes at 25° C., wherein the ratio of gum to fluid is from about 30:70 to about 70:30.

11. A shampoo composition as in claim 9, wherein said silicone conditioning agent comprises a silicone fluid and a silicone resin, wherein said silicone resin has at least about 1.1 oxygen atoms per silicon atom and is soluble in said silicone fluid, and the weight ratio of silicone fluid:silicone resin is from about 4:1 to about 400:1.

12. A shampoo composition as in claim 10, wherein said silicone conditioning agent further comprises a silicone resin that has a ratio of oxygen to silicon atoms of at least about 1.2 to 1.0 and is soluble in said silicone fluid component, and the weight ratio of silicone fluid component; silicone resin is from about 4:1 to about 400:1.

13. A shampoo composition as in claim 2 in the form of a pourable liquid.

14. A method for cleaning and conditioning the hair comprising applying an effective amount of the composition of claim 1 to the hair and then rinsing said composition from the hair.

15. A method for cleaning and conditioning the hair comprising applying an effective amount of the composition of claim 2 to the hair and then rinsing said composition from the hair.

16. A method for cleaning and conditioning the hair comprising applying an effective amount of the composition of claim 11 to the hair and then rinsing said composition from the hair.

17. A liquid hair conditioning shampoo composition as in claim 1, further comprising an anti-static agent.

18. A composition as in claim 1, comprising from about 10 to about 25%, by weight, of the artionic surfactant component.

19. A composition as in claim 1, wherein the anionic surfactant component is selected from the group consisting of alkyl sulfates, ethoxylated alkyl sulfates, and mixtures thereof.

* * * * *

UNITED STATES PATENT AND TRADEMARK OFFICE
CERTIFICATE OF CORRECTION

PATENT NO. : 5,573,709

DATED : November 12, 1996

INVENTOR(S) : Robert L. Wells

It is certified that error appears in the above-identified patent and that said Letters Patent is hereby corrected as shown below:

At column 1, line 47 "both carbonic" should read --both cationic--.

At column 4, line 34 "RO($C_2H_4O$)$_x$$SO_3$M" should read --RO($C_2H_4O$)$_x$$SO_3$M--.

At column 7, line 51 "di(2hydroxyethyl)" should read --di(2-hydroxyethyl)--.

At column 9, line 19 "the 1 like" should read --the like--.

At column 10, line 15 "silicone. hair" should read --silicone hair--.

At column 10, line 66 "irratating" should read --irritating--.

At column 10, line 67 "othewise" should read --otherwise--.

At column 11, line 67 "and and methylvinyl" should read --and methylvinyl--.

At column 13, line 48 "functional ities" should read --functionalities--.

At column 13, line 63 "functional ities" should read --functionalities--.

At column 14, line 32 "moieties" should read --moieties--.

At column 15, line 40 "methylchloroisothiazol inone" should read --methylchloroisothiazolinone--.

At column 19, line 47 "sapcosine" should read --sarcosine--.

At column 19, line 48 "sapcosine" should read --sarcosine--.

At column 20, line 6 "mixtures." should read --mixtures thereof.--.

At column 20, line 29 "component;" should read --component:--.

UNITED STATES PATENT AND TRADEMARK OFFICE
CERTIFICATE OF CORRECTION

PATENT NO. : 5,573,709
DATED : November 12, 1996
INVENTOR(S) : Robert L. Wells

It is certified that error appears in the above-indentified patent and that said Letters Patent is hereby corrected as shown below:

At column 20, line 48 "artionic" should read --anionic--.

Signed and Sealed this

Eighteenth Day of February, 1997

Attest:

BRUCE LEHMAN

*Attesting Officer*   *Commissioner of Patents and Trademarks*